United States Patent
Grass et al.

(10) Patent No.: US 9,895,117 B2
(45) Date of Patent: Feb. 20, 2018

(54) GRATING DEVICE FOR PHASE CONTRAST AND/OR DARK-FIELD IMAGING OF A MOVABLE OBJECT

(71) Applicant: KONINKLIJKE PHILIPS N.V., Eindhoven (NL)

(72) Inventors: Michael Grass, Buchholz in der Nordheide (DE); Dirk Schafer, Hamburg (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/310,933

(22) PCT Filed: Oct. 1, 2015

(86) PCT No.: PCT/EP2015/072747
§ 371 (c)(1),
(2) Date: Nov. 14, 2016

(87) PCT Pub. No.: WO2016/058838
PCT Pub. Date: Apr. 21, 2016

(65) Prior Publication Data
US 2017/0209108 A1      Jul. 27, 2017

(30) Foreign Application Priority Data
Oct. 13, 2014   (EP) ..................... 14188641

(51) Int. Cl.
*G03H 5/00* (2006.01)
*A61B 6/00* (2006.01)

(52) U.S. Cl.
CPC ............ *A61B 6/4291* (2013.01); *A61B 6/484* (2013.01); *A61B 6/503* (2013.01); *A61B 6/504* (2013.01); *A61B 6/527* (2013.01)

(58) Field of Classification Search
CPC .. G21K 2207/005; A61B 6/484; A61B 6/541; G01J 3/1833; G01N 23/20075; G01N 23/04; H05G 1/62
(Continued)

(56) References Cited

U.S. PATENT DOCUMENTS 9,492,135 B2 * 11/2016 Yamato ................. A61B 6/503
2007/0183558 A1   8/2007 Hempel
(Continued)

FOREIGN PATENT DOCUMENTS

EP        1731099       12/2006

OTHER PUBLICATIONS

Tilman Donath et al, "Inverse geometry for grating based x-ray phase contrast imaging", Journal of Applied Physics 106, 054703, 2009.

*Primary Examiner* — Jurie Yun

(57) ABSTRACT

The invention relates to a grating device for phase contrast and/or dark-field imaging of a movable object, an interferometer unit, a phase contrast and/or dark-field imaging system, a phase contrast and/or dark-field imaging method, a computer program element for controlling such device and a computer readable medium having stored such computer program element. The grating device comprises a grating unit, an actuation unit, a motion detecting unit, and a control unit. The actuation unit is configured to position the grating unit in different sampling positions relative to the moveable object. The motion detecting unit is configured to detect a motion of the movable object. The detected motion of the moveable object may be a repetitive motion. The control unit is configured to control the actuation unit to position the grating unit in the different sampling positions based on the detected motion of the movable object.

14 Claims, 3 Drawing Sheets

(58) Field of Classification Search
USPC ..................................... 378/36, 62, 95, 165
See application file for complete search history.

(56) References Cited

U.S. PATENT DOCUMENTS

| | | |
|---|---|---|
| 2010/0322380 A1 | 12/2010 | Baeumer et al. |
| 2011/0293064 A1 | 12/2011 | Huang et al. |
| 2012/0153182 A1 | 6/2012 | Iwakiri |
| 2013/0070062 A1 | 3/2013 | Fouras et al. |
| 2013/0235973 A1 | 9/2013 | Murakoshi et al. |
| 2013/0315373 A1 | 11/2013 | Rossl et al. |
| 2014/0126690 A1* | 5/2014 | Yamaguchi ............ A61B 6/484 378/36 |
| 2014/0177795 A1 | 6/2014 | Spahn |

* cited by examiner

GRATING DEVICE FOR PHASE CONTRAST AND/OR DARK-FIELD IMAGING OF A MOVABLE OBJECT

CROSS REFERENCE TO RELATED APPLICATIONS

This application is the U.S. National Phase application under 35 U.S.C. § 371 of International Application No. PCT/EP2015/072747, filed Oct. 1, 2015, published as WO 2016/058838 on Apr. 21, 2016, which claims the benefit of European Patent Application Number 14188641.6 filed Oct. 13, 2014. These applications are hereby incorporated by reference herein.

FIELD OF THE INVENTION

The invention relates to a grating device for phase contrast imaging and/or dark-field imaging of a movable object, an interferometer unit, a phase contrast and/or dark-field imaging system, a phase contrast and/or dark-field imaging method, a computer program element for controlling such device and a computer readable medium having stored such computer program element.

BACKGROUND OF THE INVENTION

While classical X-ray imaging measures absorption of X-rays caused by an object, phase contrast imaging aims at a detection of a phase shift X-rays are subjected to when they pass through an object to be examined. For phase contrast imaging and/or dark-field imaging, a phase grating is placed behind the object to generate an interference pattern of intensity maxima and minima when the object is irradiated with (coherent) X-rays. Any phase shift in the X-ray waves that is introduced by the object causes some characteristic displacement in the interference pattern. Measuring these displacements therefore allows reconstructing the phase shift of the object. Employing such phase grating, in addition the generation of image data deriving from de-coherent X-ray small angle scattering is enabled, the latter type of imaging also being referred to as "dark-field imaging".

EP 1 731 099 A1 discloses an X-ray interferometer arrangement comprising one phase grating and one amplitude grating. This interferometer can be used to obtain phase contrast images with a standard X-ray tube. Additionally, the interferometer may use a source consisting of an array of individual sub-sources. The array of sub-sources may be generated by placing an array of slits, i.e. an additional amplitude grating close to the source.

US 2010/0322380 A1 discloses hereto an X-ray detector that comprises an array of sensitive elements and at least two analyzer gratings disposed with different phase and/or periodicity in front of two different sensitive elements. The analyzer gratings with mutually different phases may be disposed in front the sensitive elements. The detector can be applied in an X-ray device for generating phase contrast images.

As a result, phase contrast imaging not only provides images showing the absorption of X-ray by the object under examination, but also additional images showing the phase shift of the X-ray beam by the object and the dark field of the object.

For phase contrast imaging, a setup with e.g. three different gratings is required. Two of those gratings are installed behind the patient and one of the two—the so-called analyzer grating—needs to be repositioned during imaging in order to sample the phase shift at various sampling positions. When performing phase contrast imaging, it is therefore assumed that the object is not moving. However, this is not an accurate assumption when imaging a moving object as e.g. parts of a coronary system or a pulmonary system.

SUMMARY OF THE INVENTION

Hence, there may be a need to provide an improved grating device for phase contrast and/or dark-field imaging which can be used in a wider application area.

The problem of the present invention is solved by the subject-matters of the independent claims, wherein further embodiments are incorporated in the dependent claims. It should be noted that the aspects of the invention described in the following apply also to the grating device for phase contrast imaging and/or dark-field imaging of a movable object, the interferometer unit, the phase contrast and/or dark-field imaging system, the phase contrast and/or dark-field imaging method, the computer program element, and the computer readable medium.

According to the present invention, a grating device for phase contrast imaging and/or dark-field imaging of a movable object is presented. The grating device comprises a grating unit, an actuation unit, a motion detecting unit, and a control unit.

The actuation unit is configured to position the grating unit in different sampling positions relative to the moveable object.

The motion detecting unit is configured to detect a motion of the movable object.

The control unit is configured to control the actuation unit to position the grating unit in the different sampling positions based on the detected motion of the movable object.

As a result, an approach for phase contrast imaging and/or dark-field imaging of moving objects is provided and the application area of phase contrast and/or dark-field imaging is widened to movable objects.

The movable object may be e.g. a heart, a lung, a muscle participating at a respiration movement, a vessel, a coronary artery, a pulmonary artery, parts of it and/or the like. This approach can also be used to achieve phase contrast stent boosting applications.

In an example, the detected motion of the moveable object is a repetitive motion. The repetitive motion of the moveable object may be a motion which brings the movable object from a starting point during one cycle back to the starting point. The motion may be e.g. a periodic, cyclic, quasi-periodic, quasi-cyclic motion or else. In an example, the detected motion of the moveable object is a cardiac cycle, a respiration cycle or a breath-hold failure during a thorax scan.

In an example, the detected motion data are at least one of the group of absorption image data, ECG data, motion sensor data, video data, combinations thereof and/or the like.

The positioning of the grating unit in the different sampling positions based on the detected motion of the movable object may be understood in that the sampling positions correspond, correlate and/or depend on the detected motion of the movable object. In other words, the invention suggests distributing the grating unit movement within e.g. a cardiac cycle or over multiple cardiac cycles.

In an example, the different sampling positions correspond to one motion state of the moveable object in different cycles of the detected motion. In other words, the grating unit movement is such that the various sampling positions correspond to one and same motion state in different cardiac cycles. This approach will be explained in more detail further below.

In an example, the different sampling positions correspond to different motion states of the moveable object in one cycle of the detected motion. In other words, the grating unit movement is such that the various sampling positions correspond to different motion states in one and same cardiac cycle. This approach will also be explained in more detail further below.

In an example, there are at least three mutually different sampling positions during one imaging run in order to acquire images at various sampling positions allowing for a phase-retrieval, i.e., the determination of the phase shift caused by the object.

In an example, the grating unit to be positioned is a grating of a Talbot interferometer and may be at least one of the group of an analyzer grating, a phase grating or a source grating. The positioning movement may be a displacement, a rotation, a tilt or combinations thereof. The analyzer grating and the phase grating may cover the complete projection or only parts of it.

The sampling positions can be distributed across a multitude of cardiac cycles and the final phase contrast image can be combined from frames acquired in different cardiac cycles using e.g. ECG correlation. In other words, ECG can be recorded generated simultaneously to correlate the various images generated at the respective grating unit positions. In an example, the control unit is therefore configured to correlate, for a phase contrast image, the detected motion of the movable object between the different sampling positions. Also the anatomy of the object to be examined, a marker on an interventional device or the like can be used for a correlation of the detected motion of the movable object between the different sampling positions.

An example of the invention is explained in the following in more detail: In cardiac X-ray fluoroscopy, a number of X-ray projections are acquired in a time series with e.g. 30 frames per second. A quasi-periodic motion of a heart brings the anatomy back to almost the same motion state in each cardiac cycle. Assuming that the motion of e.g. an analyzer grating as grating unit is slow compared to the cardiac motion, it will be impossible to acquire all projections with different analyzer grating positions in the same motion state of the heart in a single cardiac cycle. Thus, phase stepping, which is image acquisition at regular phase intervals by shifting e.g. the analyzer grating in uniform steps, can be distributed across a multitude of cardiac cycles and the final phase contrast image (and the dark field image) can be obtained from projections acquired in different cardiac cycles using e.g. ECG correlation. In other words, ECG can be recorded simultaneously to correlate the various projections generated at the respective analyzer grating positions.

The so-called "different cycles approach" can be performed as follows: A sequence of phase contrast projections of the heart can be acquired and an ECG can be measured in parallel. The phase stepping can be chosen in a way that the analyzer grating as grating unit is in a different sampling position when acquiring the same cardiac motion state in subsequent cardiac cycles. The phase contrast and dark field image can be obtained (calculated) from projections acquired in different cardiac cycles.

For the phase stepping, the sampling positions of the grating unit should be different and non-redundant. Herein, non-redundant means that the position of the analyzer grating relative to the phase grating is different for each of the sampling positions. As only the sampling positions are relevant for the phase stepping, the phase stepping can be aligned to the mean heart rate and small variations in the cycle length do not affect the resulting images.

The actual motion state of the heart can be determined prior to calculating the phase contrast and dark field images by checking the correspondence of the motion state via the absorption image. Thus, measured frames can be selected, which correspond well with respect to the spatial position of the heart.

The alternative "one cycle approach" to achieve motion corrected phase contrast images can be based on image based registration on the absorption projections prior to calculating the phase contrast and dark field images. With this approach, a sequence of e.g. three subsequently acquired projections with different grating unit positions can be used to generate the phase contrast image and dark field image. The motion which can occur in-between these projections during e.g. the cardiac motion can be estimated from the partial absorption images and thus can be corrected prior to the calculation of the final images. The motion of the heart in between sampling positions can be compensated based on the absorption images.

Exemplarily, also alternative motion sensors are imaginable as video signals like e.g. the output of a vital signs camera.

According to the present invention, also an interferometer unit is presented. The interferometer unit comprises an X-ray detector and the grating device for phase contrast and/or dark-field imaging of a movable object as described above. The X-ray detector is configured to detect an X-ray beam passing the grating device. The grating device comprises a grating unit, an actuation unit, a motion detecting unit, and a control unit. The grating unit is positioned in different sampling positions based on the detected motion of the movable object. The X-ray detector may be provided with pitch sufficiently small, hence a resolution sufficiently large, for detecting i.e. adequately resolving the interference pattern generated by the grating device. For that purpose the X-ray detector may be a high resolution X-ray detector known per se having a spatial resolution of 50 micrometers or more, or an X-ray detector of the type as described in US 2014/0177795 A1 which is incorporated herein by reference. Alternatively, if the grating unit is provided with an analyzed grating arranged in the optical path in front of the X-ray detector, the X-ray detector may have a less high resolution.

According to the present invention, also a phase contrast and/or dark-field imaging system is presented. The phase contrast and/or dark-field imaging system comprises an X-ray source and the interferometer unit as described above. The X-ray source is configured to provide an X-ray beam to pass through an object and the interferometer unit. The phase contrast and/or dark-field imaging system allows a phase contrast and/or dark-field imaging of moving objects. The movable object may be e.g. a heart, a lung, a muscle participating at a respiration movement, a vessel, a coronary artery, a pulmonary artery and/or parts of it.

According to the present invention, also a phase contrast and/or dark-field imaging method is presented. It comprises the following steps, not necessarily in this order:
a) detecting a motion of a movable object, and
b) controlling a positioning of a grating unit in different sampling positions relative to the moveable object based on the detected motion of the movable object.

In an example, the detected motion of the moveable object is a repetitive motion. The repetitive motion may be e.g. a periodic, cyclic, quasi-periodic or quasi-cyclic motion. The repetitive motion of the moveable object may be a motion which brings the movable object from a starting point during one cycle back to the starting point. In an example, the detected motion of the moveable object is a cardiac cycle or a respiration cycle.

In an example, the different sampling positions correspond to one motion state of the moveable object in different cycles of the detected motion. In another example, the different sampling positions correspond to different motion states of the moveable object in one cycle of the detected motion.

According to the present invention, also a computer program element is presented, wherein the computer program element comprises program code means for causing a grating device as defined in the independent device claim to carry out the steps of the phase contrast and/or dark-field imaging method when the computer program is run on a computer controlling the grating device.

It shall be understood that the grating device, the interferometer unit, the phase contrast and/or dark-field imaging system, the phase contrast and/or dark-field imaging method, the computer program element for controlling such device and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
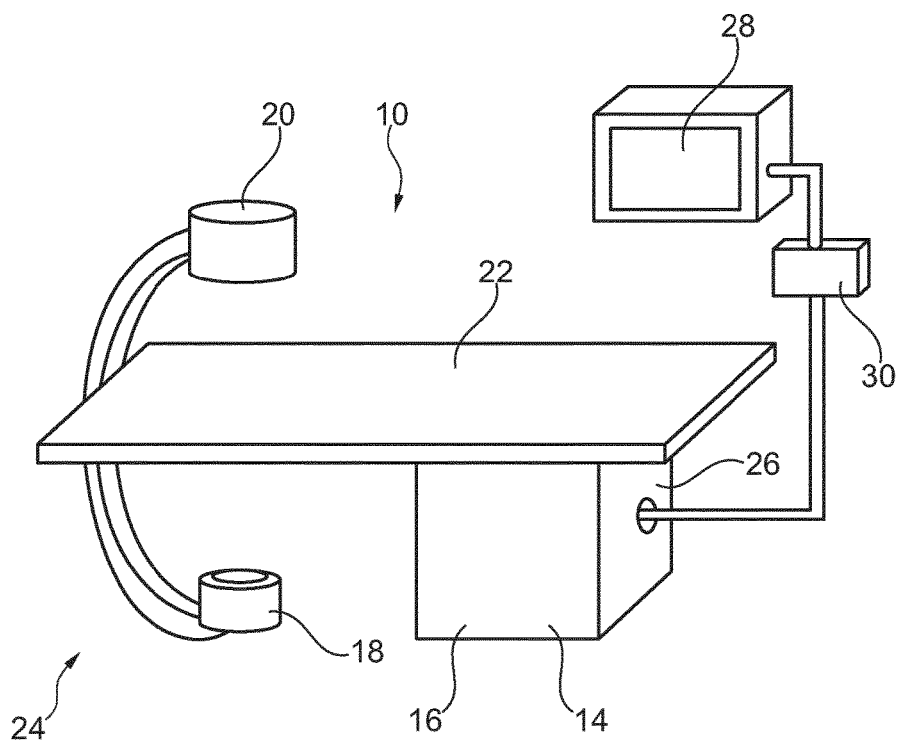
FIG. 1 shows a schematic drawing of an example of a phase contrast and/or dark-field imaging system for differential phase-contrast imaging of a movable object according to the invention.

In FIG. 1, a phase contrast and/or dark-field imaging system 10 for differential phase-contrast imaging is schematically shown. The phase contrast and/or dark-field imaging system 10 comprises an X-ray source 18, an interferometer unit 20, a processing unit 14 and an interface unit 16. The interferometer unit 20 will be explained in detail to FIG. 2 and comprises a grating device and a detector adapted to record intensity variations of X-ray radiation. The grating device comprises a grating unit, which can be e.g. an analyzer grating, a phase grating or a source grating.

A table 22 is arranged to receive an object to be examined (not shown). The X-ray source 18 and the interferometer unit 20 are at least partially mounted on a C-arm device 24 such that the table 22 can be arranged between the X-ray source 18 and the interferometer unit 20, so that the object can be placed between the X-ray source 18 and the interferometer unit 20.

The C-arm device 24 is provided such that a movement of the C-arm device 24 around the object is possible to be able to adapt the viewing direction. Further, a base 26 is provided on which the table 22 is mounted. The base 26 is located, for example, on the floor of an examination room. As an example, the processing unit 14 and the interface unit 16 are provided within the base 26. Further, a display 28 is arranged in the vicinity of the table 22 to provide information to the user, for example a surgeon. An interface unit 30 is arranged to provide the possibility to further control the system.

The object, for example a patient, can be located between the X-ray source 18 and the interferometer unit 20 during the radiation procedure. The interferometer unit 20 is sending data to the processing unit 14 via the interface unit 16 to provide the detected raw image data to the processing unit 14. Of course, the processing unit 14 and the interface unit 16 can be located at other locations, e.g. at a different laboratory room or a control room.

Further, it is noted that the example shown is a so-called C-type X-ray image acquisition device. Of course, other X-ray image acquisition devices can be provided, for example CT systems and stationary systems with fixed or movable X-ray source 18 and interferometer units 20. Of course, also movable X-ray devices can be provided.

Figure 2:
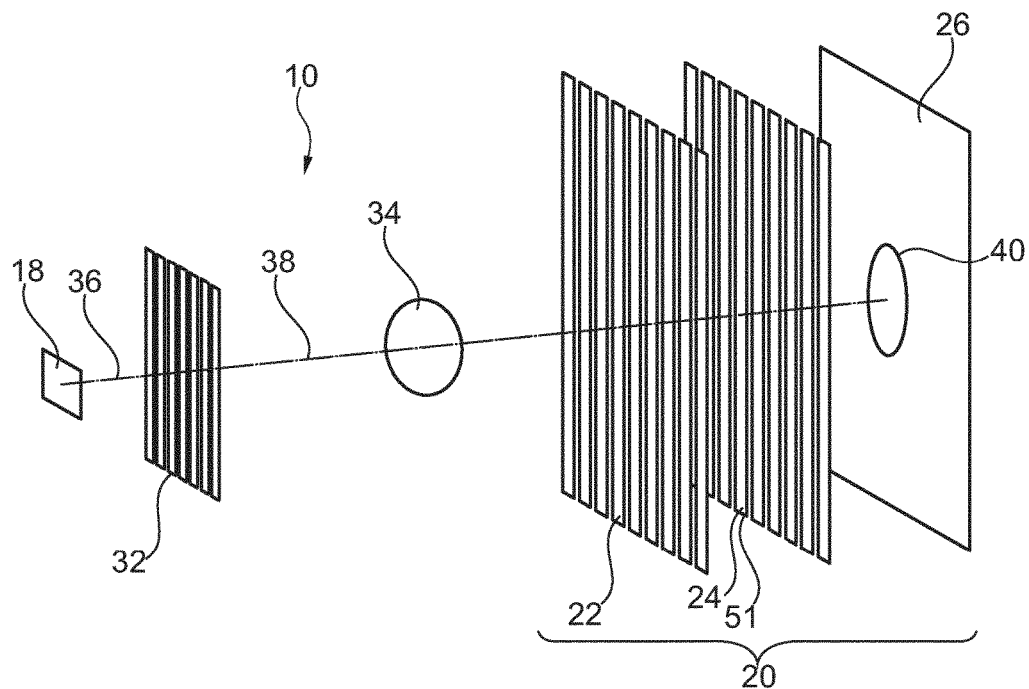
FIG. 2 shows schematically and exemplarily an embodiment of an interferometer unit for differential phase-contrast imaging of a movable object according to the invention.

FIG. 2 shows schematically the interferometer unit 20 comprising a grating device and a detector 26 to record intensity variations of X-ray radiation. The grating device, as explained in detail in FIG. 3, comprises a grating unit 51, which is here an analyzer grating 24. FIG. 2 further shows an X-ray source 18, a source grating 32 and a phase grating 22. Further, an object 34 is schematically indicated in FIG. 2.

The X-ray source 18 generates an X-ray beam 36 of a polychromatic spectrum. In order to provide sufficient coherence to the X-ray beam 36 applied to the object 34, the source grating 32 is adapted with a respective grating structure to split the X-ray radiation of the X-ray source 18 to at least partially coherent X-ray radiation. Thus, the X-ray beam 36 passes the source grating 32 and is then provided as an adapted X-ray beam 38. As a consequence, interference can be observed at the location of the analyzer grating 24.

In the specific example displayed in FIG. 2, the source grating 32, the phase grating 22 and the analyzer grating 24 are arranged in a so-called "conventional geometry". In said conventional geometry the distance between the source grating 32 and the phase grating 22 is larger than the distance between the phase grating 22 and the analyzer grating 24. Alternatively, the source grating 32, the phase grating 22 and the analyzer grating 24 may be arranged in a so-called "inverse geometry". In said inverse geometry the distance between the source grating 32 and the phase grating 22 is smaller than the distance between the phase grating 22 and the analyzer grating 24. Consequently, in the inverse geometry, the object to be imaged is typically arranged between the phase grating 22 and the analyzer grating 24. As another option, the source grating 32, the phase grating 22 and the analyzer grating 24 may be arranged in a so-called "symmetric geometry". In said inverse geometry the distance between the source grating 32 and the phase grating 22 equals the distance between the phase grating 22 and the analyzer grating 24. For more information (incorporated herein by reference) see Tilman Donath et al, "Inverse geometry for grating based x-ray phase contrast imaging", JOURNAL OF APPLIED PHYSICS 106, 054703, 2009.

According to a further exemplary embodiment, although not further shown, the source grating can be omitted and the X-ray source 18 is adapted to provide sufficient coherent X-ray radiation, so that interference can be observed at the location of the analyzer grating 24, for example by synchrotron or microfocus X-ray tubes.

According to a further exemplary embodiment, although not further shown, the grating unit 51 can also be the phase grating 22 or the source grating 32.

In FIG. 2, it is shown that the source 18, the source grating 32, the phase grating 22, and the analyzer grating 24 as well as the detector 26 are arranged along an optical path. The detector 26 thus records image information 40 of the object 34.

Figure 3:
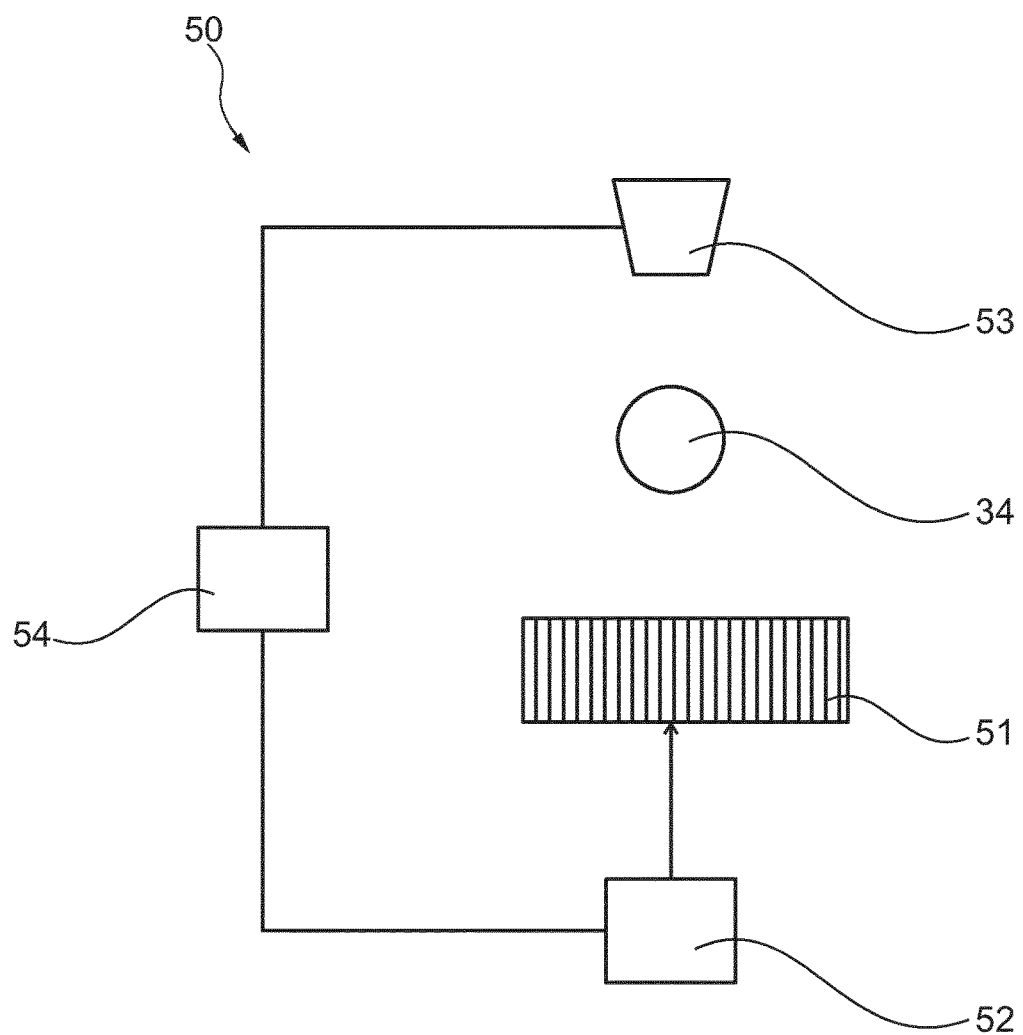
FIG. 3 shows schematically and exemplarily an embodiment of a grating device for phase contrast and/or dark-field imaging of a movable object according to the invention.

FIG. 3 shows schematically and exemplarily an embodiment of a grating device 50 for phase contrast and/or dark-field imaging of a movable object 34 according to the invention. The grating device 50 comprises a grating unit 51, an actuation unit 52, a motion detecting unit 53, and a control unit 54. The actuation unit 52 positions the grating unit 51 in different sampling positions relative to the moveable object 34. The motion detecting unit 53 detects the motion of the movable object 34. The detected motion of the moveable object 34 is here a repetitive motion. The control unit 54 controls the actuation unit 52 to position the grating unit 51 in the different sampling positions based on the detected motion of the movable object 34. Thereby, a grating device 50 for phase contrast and/or dark-field imaging of moving objects 34 is provided.

The movable object 34 may be e.g. a heart, a lung, a muscle participating at a respiration movement, a vessel, a coronary artery, a pulmonary artery and/or parts of it. The motion may be e.g. a periodic, cyclic, quasi-periodic or quasi-cyclic motion. The motion data may be at least one of the group of absorption image data, ECG data, motion sensor data and video data. The grating unit 51 is here an analyzer grating 24. The motion detecting unit 53 may be an ECG. In this case, the motion detecting unit 53 is not arranged on the moveable C-arm device 24.

Figure 4:
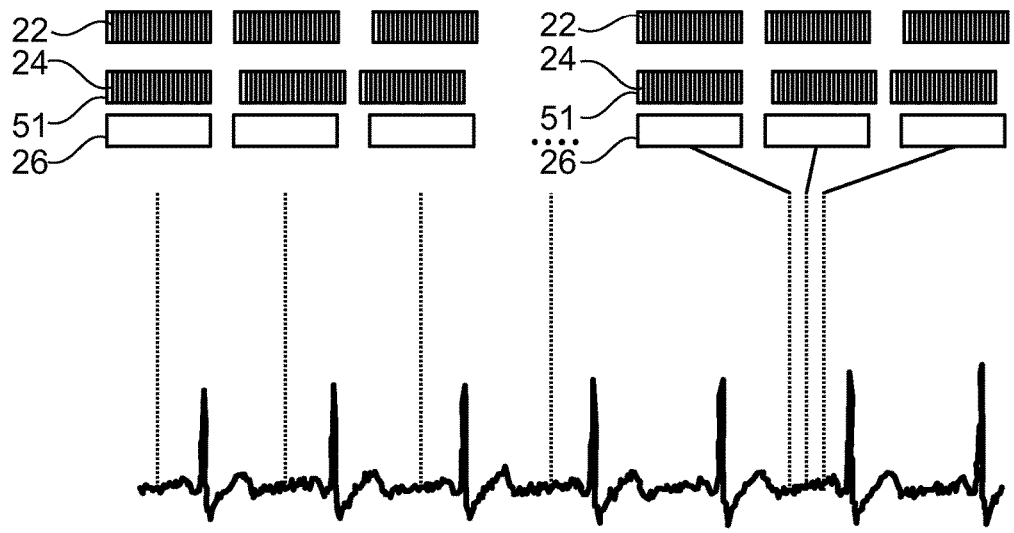
FIG. 4 shows a schematic representation of an electrocardiogram and a phase contrast setup with an analyzer grating in different sampling positions.

The invention suggests distributing the grating unit 51 movement within one cycle of the motion or over multiple cycles of the motion. FIG. 4 shows a schematic representation of an electrocardiogram and a phase contrast setup with the analyzer grating 24 in different sampling positions in the same motion state in different cardiac cycles (left) as well as a phase contrast setup with the analyzer grating 24 in different sampling positions for three different projections acquired in the same cardiac cycle (right). FIG. 4 further shows the constantly positioned phase grating 22 and detector 26.

In the example on the left of FIG. 4, the different sampling positions correspond to one motion state of the moveable object 34 in different cycles of the detected motion. In other words, the grating unit 51 movement is such that the various sampling positions correspond to one and same motion state in different cardiac cycles. The so-called "different cycles approach" is performed in that a sequence of phase contrast projections of the heart is acquired and e.g. an ECG is measured in parallel. The phase stepping is chosen in a way that the analyzer grating 24 is in a different sampling position when acquiring the same cardiac motion state in subsequent cardiac cycles. The phase information from frames acquired in different cardiac cycles is then combined based on the ECG information.

In the example on the right of FIG. 4, the different sampling positions correspond to different motion states of the moveable object 34 in one cycle of the detected motion. In other words, the grating unit 51 movement is such that the various sampling positions correspond to different motion states in one and same cardiac cycle. The so-called "one cycle approach" to achieve motion corrected phase contrast images can be based on image based registration on the absorption projections prior to calculating the phase contrast and dark field images. With this approach, a sequence of e.g. three subsequently acquired images with different grating unit positions is used to generate the phase image and dark field image. The motion which can occur in-between these images during the cardiac motion is estimated from the partial absorption images and is thus corrected prior to the calculation of the final images. The motion of the heart in between sampling positions is then compensated based on the absorption images.

Figure 5:
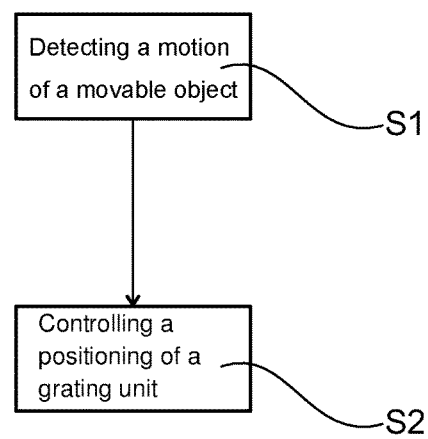
FIG. 5 shows basic steps of an example of a phase contrast and/or dark-field imaging method.

FIG. 5 shows a schematic overview of steps of a phase contrast and/or dark-field imaging method. The method comprises the following steps, not necessarily in this order:

In step S1 detecting a motion of a movable object 34, and

In step S2 controlling a positioning of a grating unit 51 in different sampling positions relative to the moveable object 34 based on the detected motion of the movable object 34

The phase contrast and/or dark-field imaging method allows a phase contrast and/or dark-field imaging of moving objects 34. The movable object 34 may be e.g. a heart, a lung, a muscle participating at a respiration movement, a vessel, a coronary artery, a pulmonary artery and/or parts of it. The motion may be a repetitive motion. The motion may be e.g. a periodic, cyclic, quasi-periodic or quasi-cyclic motion. In an example, the detected motion of the moveable object 34 is a cardiac cycle or a respiration cycle.

In an example, the different sampling positions correspond to one motion state of the moveable object 34 in different cycles of the detected motion. In another example, the different sampling positions correspond to different motion states of the moveable object 34 in one cycle of the detected motion.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is provided wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A grating device for phase contrast imaging and/or dark-field imaging of a movable object comprising:
   a grating unit,
   an actuation unit,
   a motion detecting unit, and
   a control unit,
   wherein the actuation unit is configured to position the grating unit in different sampling positions relative to the moveable object,
   wherein the motion detecting unit is configured to detect a motion of the movable object,
   wherein the control unit is configured to control the actuation unit to position the grating unit in the different sampling positions based on the detected motion of the movable object.

2. The grating device according to claim 1, wherein the detected motion of the moveable object is a repetitive motion.

3. The grating device according to claim 1, wherein the detected motion of the moveable object is a cardiac cycle or a respiration cycle.

4. The grating device according to claim 1, wherein the different sampling positions correspond to one motion state of the moveable object in different cycles of the detected motion.

5. The grating device according to claim 1, wherein the different sampling positions correspond to different motion states of the moveable object in one cycle of the detected motion.

6. The grating device according to claim 5, wherein the control unit is configured to correlate, for a phase contrast image, the detected motion of the movable object between the different sampling positions.

7. The grating device according to claim 6, wherein data of the detected motion are at least one of the group of absorption image data, ECG data, motion sensor data and video data.

8. The grating device according to claim 1, wherein the grating unit is a grating of a Talbot interferometer.

9. The grating device according to claim 1, wherein there are at least three mutually different sampling positions during one imaging run.

10. An interferometer unit comprising:
    a grating device according to claim 1; and
    an X-ray detector;
    wherein the X-ray detector is configured to detect an X-ray beam passing the grating device.

11. A phase contrast and/or dark-field imaging system, comprising:
    an interferometer unit according to claim 10; and
    an X-ray source;
    wherein the X-ray source is configured to provide an X-ray beam to pass through the interferometer unit.

12. A phase contrast and/or dark-field imaging method, comprising the steps of:
    a) detecting a motion of a movable object, and
    b) controlling a positioning of a grating unit in different sampling positions relative to the moveable object based on the detected motion of the movable object.

13. A non-transitory computer program element for controlling a device, which, when being executed by a processing unit, is adapted to perform the method steps of claim 12.

14. A non-transitory computer readable medium having stored the program element of claim 13.

* * * * *